United States Patent
Herzog et al.

(10) Patent No.: US 11,292,004 B2
(45) Date of Patent: Apr. 5, 2022

(54) METHOD AND DEVICE FOR METERING AND STORING LIQUIDS BY MEANS OF PERMANENTLY OPEN CONTAINERS

(71) Applicant: Aquila Biolabs GmBH, Baesweiler (DE)

(72) Inventors: Konrad Herzog, Baesweiler (DE); David Frank, Baesweiler (DE); Carsten Presser, Baesweiler (DE)

(73) Assignee: Aquila Biolabs GmBH, Baesweiler (DE)

( * ) Notice: Subject to any disclaimer, the term of this patent is extended or adjusted under 35 U.S.C. 154(b) by 0 days.

(21) Appl. No.: 16/313,828

(22) PCT Filed: Mar. 2, 2018

(86) PCT No.: PCT/EP2018/055176
§ 371 (c)(1),
(2) Date: Dec. 27, 2018

(87) PCT Pub. No.: WO2018/158431
PCT Pub. Date: Sep. 7, 2018

(65) Prior Publication Data
US 2019/0224681 A1   Jul. 25, 2019

(30) Foreign Application Priority Data
Mar. 3, 2017   (DE) ..................... 10 2017 002 046.9

(51) Int. Cl.
*B01L 3/00*   (2006.01)
*C12M 1/26*   (2006.01)
(Continued)

(52) U.S. Cl.
CPC ................. *B01L 3/52* (2013.01); *B01L 3/523* (2013.01); *B01L 3/567* (2013.01); *B05B 9/03* (2013.01);
(Continued)

(58) Field of Classification Search
CPC ... B05B 9/03; B01L 3/52; B01L 3/523; B01L 3/567; B01L 2200/146; B01L 2200/147;
(Continued)

(56) References Cited

U.S. PATENT DOCUMENTS 4,116,778 A * 9/1978 Belousov ............... C12M 41/36
435/287.1
7,396,512 B2 * 7/2008 DiTrolio ................. B01L 3/021
422/522
(Continued)

FOREIGN PATENT DOCUMENTS

DE   10 2011 078 855 A1   1/2013
DE   10 2016 000 997 B3   2/2017
(Continued)

OTHER PUBLICATIONS

PCT/EP2018/055176 International Search Report dated Jun. 26, 2018.

*Primary Examiner* — Liban M Hassan
(74) *Attorney, Agent, or Firm* — Wagenknecht IP Law Group PC

(57) ABSTRACT

A method for metering and storing liquids by means of a permanently open container (1), wherein: the container (1) comprises a liquid reservoir (11) in which at least one liquid (2) is contained for storage; the container (1) has at least one opening (15) for the metered discharging of the liquid from the liquid reservoir (11); the opening (15) is permanently open; influencing factors affect at least one change in pressure (4) in the container (1); influencing factors render the system formed of the container (1) and liquid (2) unstable; the pressure (4) is detected in at least one location in the container (1); and, subject to at least one detected change in pressure (4), at least one reaction (9) is initiated that is suitable for maintaining the system of the container
(Continued)

(1) and liquid (2) in a stable state or for re-establishing this stable state.

32 Claims, 4 Drawing Sheets

(51) Int. Cl.
    *C12M 1/34*     (2006.01)
    *C12M 1/36*     (2006.01)
    *B05B 9/03*     (2006.01)

(52) U.S. Cl.
    CPC ............ *C12M 33/04* (2013.01); *C12M 41/40* (2013.01); *C12M 41/48* (2013.01); *B01L 2200/0605* (2013.01); *B01L 2200/146* (2013.01); *B01L 2200/147* (2013.01); *B01L 2300/049* (2013.01); *B01L 2300/0663* (2013.01); *B01L 2300/14* (2013.01); *B01L 2400/0487* (2013.01)

(58) Field of Classification Search
    CPC ......... B01L 2200/0605; B01L 2300/14; B01L 2300/049; B01L 2300/0663; B01L 2400/0487; C12M 33/04; C12M 41/40; C12M 41/48
    USPC ......... 435/286.5, 287.1, 289.1, 39, 808, 813
    See application file for complete search history.

(56) References Cited

U.S. PATENT DOCUMENTS

2006/0159593 A1\*   7/2006   Torisawa ............... G01N 35/10
                                                      422/400
2013/0064738 A1\*   3/2013   Berger .................... B01J 4/002
                                                      422/521

FOREIGN PATENT DOCUMENTS

| EP | 2 492 658 A1 | 8/2012 |
|----|--------------|--------|
| JP | H02 184370 A | 7/1990 |
| WO | 2005/099906 A1 | 10/2005 |

\* cited by examiner

METHOD AND DEVICE FOR METERING AND STORING LIQUIDS BY MEANS OF PERMANENTLY OPEN CONTAINERS

CROSS REFERENCE TO RELATED APPLICATIONS

This is a US national phase application under 35 USC § 371 of international patent application no. PCT/EP2018/055176, filed Mar. 2, 2018, which claims priority to German patent application no. DE 10 2017 002 046.9, filed Mar. 3, 2017, the content of each is herein incorporated by reference in its entirety.

TECHNICAL FIELD

The invention relates to a method and a device for metering and storing liquids by means of permanently open containers. The invention applies in particular to the metering and storing of liquids used for biological and chemical processes that run for hours or days. Furthermore, it may be applied anywhere the liquid to be metered or stored as well as its container are exposed to temperature changes or jolting.

BACKGROUND OF THE INVENTION

Permanently open containers are often used for metering liquids in various areas of biological or chemical work and processes. Some of the most common types of containers are syringes and pipettes. These are characterized by at least one permanently open metering opening and have the characteristic that the liquid contained in them remains in the container when at least one metering opening is covered by liquid. What is causal for this is a balance from the ambient air pressure, the hydrostatic pressure of the liquid, the pressure in the container, and surface and capillary effects.

This balance can, however, be influenced by external factors, which may lead to a rather negative change in the fluid distribution, in particular due to the loss of liquid through at least one container opening or due to a change in the fluid distribution within the container (e.g., due to suctioning). First of all, this leads to undesired metering processes and, secondly, to a negative loss in metering precision. Significant external influencing factors are jolting or otherwise unintended accelerations of the liquid toward the metering opening, as well as thermodynamic or chemical processes, which cause a change in the volume or pressure in the container. Changes to the surface characteristics of the container or its content must also be mentioned as influencing factors.

PRIOR ART

No methods or devices are known from prior art that solve the problem described above while maintaining the basic characteristic of permanently being open. Known methods and devices circumvent the problem by temporarily closing the container (e.g., screw caps for syringes, hose clamps, etc.). Closure devices require, however, either the use of controllable closing mechanisms (such as valves) or a manual closure which, under certain circumstances, may be impossible, or at least difficult, to do.

Consequently, no methods or devices are known which, on the one hand, maintain the advantages of permanently open containers for the metering and storing of liquids (in particular their simplicity, ease of handling, production costs, sterilizability, usability as a single-use product) and, on the other, address the problem of a shift in the balance of the liquid distribution in the container that the permanent opening causes.

SUMMARY OF THE INVENTION

It is therefore the task of the present invention to provide a method by means of which the metering and storing of liquids in a permanently open container can be performed in a robust manner without the influencing factors of loss of liquid or loss of metering precision.

According to the invention, the task is solved by the monitoring of the pressure conditions in the container as well as by an appropriate response to the detected pressure changes. The basis of the invention is the insight that every influencing factor that causes a negative distribution change in the liquid in the container causes a change of the pressure conditions in the container. By detecting this pressure change, an appropriate reaction is then initiated which counteracts the change in the liquid distribution in the container. Consequently, independently from thermodynamic, mechanical, or chemical influencing factors, a loss of liquid or metering precision is counteracted in permanently open containers as well.

According to the invention, the pressure in the container is monitored by at least one pressure sensor which transmits the pressure data detected by the sensor to at least one control unit which initiates at least one appropriate reaction to counteract the change in the fluid distribution in the container.

In some embodiments of the invention, the detection of pressure changes is performed by a number of pressure sensors at different positions.

In a preferred embodiment of the invention, not only liquid but also a gaseous component is in the container. The gas phase of the container content is, in a preferred embodiment, more compressible than the liquid phase. This allows in particular for the detection of pressure changes only by means of the gas phase so that, in the preferred embodiment of the invention, there is no direct contact between the liquid in the container and at least one pressure sensor.

In a preferred embodiment of the invention, the targeted movement or redistribution of the liquid in the container is performed by the movement of a gas phase, in particular air. According to the invention, the targeted movement or redistribution of the liquid in the container is both part of the normal metering process and of the reaction process in response to detected pressure changes in the container.

In a preferred embodiment of the invention, and in particular when a gas phase is used for the targeted movement or redistribution of the liquid in the container, the container consists of at least two components which, in some embodiments of the invention, can be joined or separated by the user of the device. In a preferred embodiment of the invention, the at least two-part container consists of at least one liquid reservoir and a metering device, whereby it is the responsibility of the liquid reservoir to store the liquid to be metered across the entire metering process and whereby the metering device facilitates the controlled discharge of liquid from the liquid reservoir within the context of at least one metering step.

In a preferred embodiment of the invention, the liquid reservoir and the metering device are joined in a gas-tight manner.

By using a container comprised of several components according to the invention in combination with the indirect movement or redistribution of the liquid by means of a gas phase, a preferred embodiment of the invention makes it possible that conditions are maintained in particular by a compartmentalization or the use of suitable materials in the liquid reservoir which cannot be maintained outside of the liquid reservoir. A condition that is particularly important in biological application is sterility.

In some embodiments of the invention, a sterility barrier (e.g., a sterile filter) is inserted in particular between the liquid reservoir on the one hand and the pressure sensor and/or the liquid transport device (7) on the other so that the sterility conditions in the liquid reservoir can be maintained.

In some embodiments of the invention, the metering devices may be used more than once while the liquid reservoir can only be used once and must be replaced prior to every new metering process. This is advantageous especially in the area of biological applications because single-use liquid reservoirs are already presterilized by the user of the device according to the invention, which means that the required sterility conditions in the liquid reservoir may be maintained in a user-friendly manner.

In embodiments that comprise a compartmentalization of the liquid container by appropriate barrier devices, the detection of at least one pressure difference in the container is performed in a preferred embodiment of the invention by at least one pressure sensor in that the pressure sensor is located behind the barrier and therefore outside of the liquid reservoir.

In a preferred embodiment of the invention, pressure changes are detected by at least one pressure sensor with measurement frequencies that are so high (e.g., >10 Hz, >100 Hz, >1000 Hz) that even correspondingly fast pressure changes as they occur for example due to jolting during transport or the installation of filled devices according to the invention can be adequately addressed.

In a preferred embodiment of the invention, at least one pressure sensor is positioned so that it is not influenced by movements that do not have a negative effect on the distribution of the liquid in the container or that it acts upon background signals. In particular, but not exclusively, the position of at least one pressure sensor in a preferred embodiment of the invention for shaken systems is such that the sensitive element of the sensor (e.g., the membrane, resistance bridge, Piezo crystal, etc.) is positioned orthogonal to the jolting level with its sensory preferred mechanical orientation.

In some embodiments of the invention, not only the pressure but also further parameters are detected and monitored as well which are capable of identifying influencing factors and their direct or indirect effect on the distribution of the liquid in the container and to initiate appropriate reactions. These parameters, which can be detected in addition to the pressure in the container, are in particular, but not exclusively, the ambient pressure of the container, the temperature of the container, its content or individual components of its content, the movement, acceleration, position, or location of the container, its content or individual components of its content, the fill level of the container, and the distribution of the liquid in the container. According to the invention, sensors that can be used for this purpose are in particular all types of pressure sensors, temperature sensors, acceleration, position, location, or rotation sensors, as well as optical, acoustic, capacitive, and resistive fill level sensors.

In some embodiments of the invention, the volume of the fluid in the container is calculated from the detected pressure values as well as any further values available.

In some embodiments of the invention, detected pressure values and any other values that are available are used to make predictions about any future liquid distributions to be expected. This is in particular, but not exclusively, advantageous for initiating preventive reactions which can in particular alleviate or prevent the negative effect of quickly changing influencing factors on the distribution of the liquid in the container in an anticipatory manner. In a preferred embodiment of the invention, prediction methods such as Kalman filters or other Bayesian estimation measurements as well as regression and extrapolation methods are used for this purpose.

In a preferred embodiment of the invention, the reaction to at least one detected pressure change in the container comprises the complete or at least substantial reconstruction of the pressure that prevailed in the container prior to the pressure changes, thereby counteracting or reversing a change in the liquid distribution. These kinds of reactions include in particular, but not exclusively, the introduction or removal of liquid in the or from the container as well as the heating or cooling of the container, its content, or individual components of its content.

In some embodiments of the invention, the reaction to at least one pressure change to be expected in the reactor in the future or acceleration of the liquid is performed preventively, in particular to weaken or eliminate the effect of such influencing factors which cause liquid distribution and pressure changes that are so fast that these can no longer be detected by at least one pressure sensor so that no adequately recoupled reaction can be initiated by the control unit anymore.

In some exemplary embodiments of the invention, the pressure is detected and/or the reaction initiated and/or the fluid discharged while the receptacle is being shaken. The method according to the invention is therefore performed in particular at the same time and continuously during the process in the receptacle. The device or the container, respectively, together with the metering device are shaken together with the container.

In particular, the device closes the receptacle, whereby in particular a lid of the container covers the receptacle as well.

The present invention is explained in further detail with the help of the figures and the exemplary embodiments.

DETAILED DESCRIPTION OF PREFERRED EMBODIMENTS

Definitions

Figure 1:
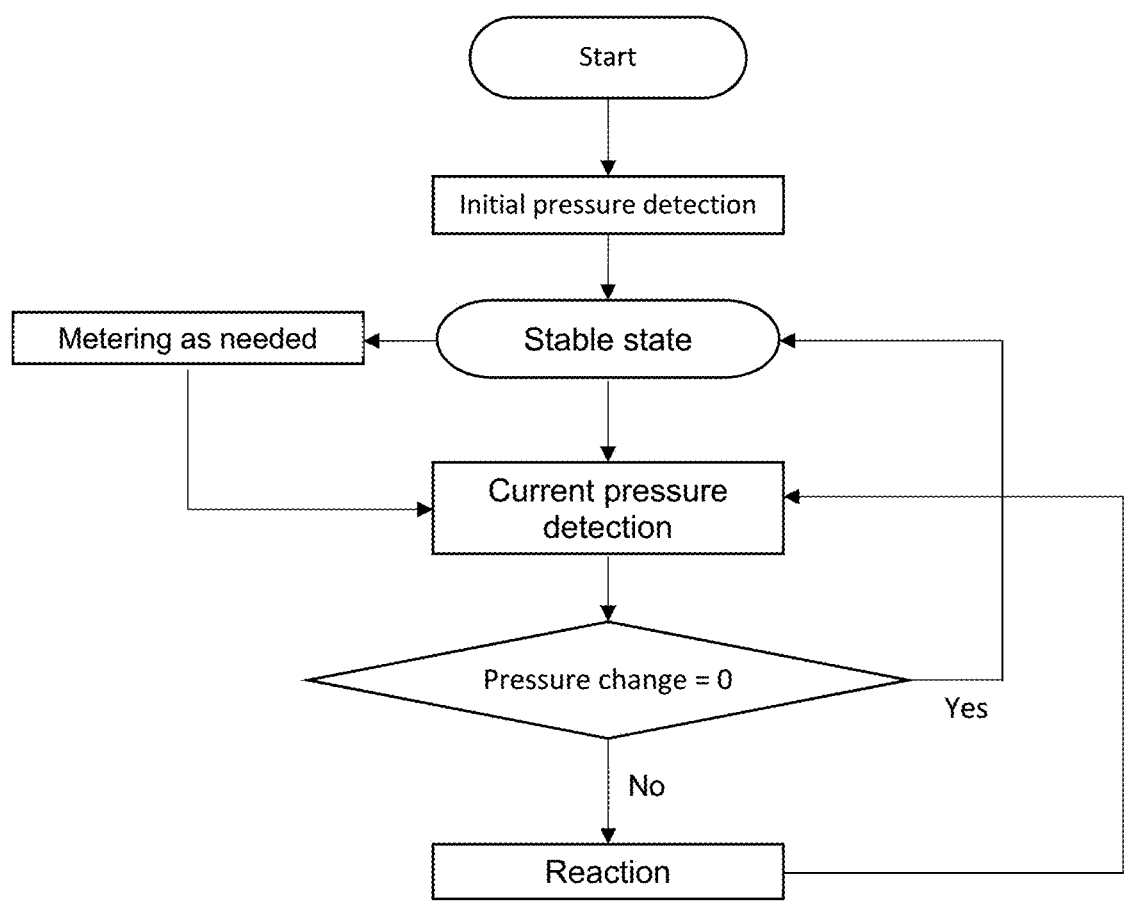
FIG. 1 shows a schematic flowchart of the method according to the invention.

To ensure that some of the terms used in the specification are clear, these will be defined and explained below and over the course of the specification.

According to the invention, a container is a receptacle that is capable of storing or metering liquid. Containers may be either closed or open to their environment. Containers according to the invention are characterized in particular by at least one permanent opening which permits the metering of liquid from the container. In many cases, and especially when the metering is performed in the form of falling drops, the permanent opening is, at the same time, the lowest point of the container so that, when the container is filled, liquid is permanently above the opening. According to the invention, a container may also consist of a number of parts. A container ends along its walls as well as at openings along the smallest or most direct area to the closure of this opening.

Influencing factors within the meaning of the invention are all physical, chemical, or biological phenomena or effects, which in particular, but not exclusively, lead to a change of the distribution or the volume of the liquid in the container, to a change of the movement state of the liquid in the container, or to a change in the pressure conditions in the container.

Reactions within the meaning of the invention are all methods or processes that are able to maintain or restore the stable state of the system according to the invention, or to at least approximate the current state to the stable state. Reactions are able to be parameterized and can be monitored and controlled. Reactions always comprise a defined number of actions, which means they have a beginning and an end. Typical reactions include in particular, but not exclusively, the opening or closing of a valve, the conveyance or the changing of the conveyance direction of a pump, or the changing of temperatures by heating or cooling. Subsequent to a reaction or during reaction, the current system state is detected and verified after a defined or undefined period of time to assess the reaction and its consequences.

Methods for the metering and storing of liquids by means of permanently open containers are, within the meaning of the invention, controlled by at least one control unit. Consequently, control units are all devices that are capable of initiating or controlling reactions for the maintenance or restoration of the stable state of a system according to the invention depending on the detected pressure values or the values of other parameters. Depending on the method used, control units within the meaning of the invention are in particular, but not exclusively, operational amplifiers, comparators, PID controllers, Schmitt triggers and computers. A computer is any electronic device that can store the data (in particular arithmetic and logical data) and process it on the basis of programmable rules. Computers within the meaning of the invention are in particular, but not exclusively, microcontrollers, microprocessors, system-on-a-chip computers (SoC), PCs, and servers.

Liquids within the meaning of the invention are pure or mixed substances that are not gases and that have fluidic characteristics. Liquids within the meaning of the invention are therefore in particular, but not exclusively, liquid phases of pure substances, solutions, emulsions, dispersions, slurries, suspensions, and foams. Due to their behavior that can be macroscopically compared to fluids, fine, pourable powders and powdered mixes are included in the term liquid as well.

According to the invention, liquids are metered from containers. Metering within the meaning of the invention refers to any process that is capable of releasing liquid from a container in a specified manner. Metering is performed by at least a controlled fluid transportation device, whereby said device works either passively (e.g., opening/closing of a valve) or actively (e.g., fluid conveyance by a pump). Metering as needed comprises within the meaning of the invention all controlled metering processes, in particular those that were preprogrammed by users (e.g., time-dependent dosing profiles), that are performed by a direct user interaction (e.g., push of a button), or that are controlled by the detection of certain parameters or process variables (e.g., cell count, pH, foam, product volume, educt volume, etc.). Metering steps are discrete metering units such as a single drop, a rotation of the pump motor, or an opening and closing process of a valve.

According to the invention, a system refers to the totality of a number of components in a shared environment, in particular the system of the device with liquid according to the invention. Every system is in a certain state or system state at any time which is characterized by different, sometimes location-dependent parameters in particular, but not exclusively, by the pressure, temperature, volume, acceleration, position, and location.

The term stable state, according to the invention, refers to all states in which no fluid is discharged from the container and from which it is possible to provide dosages that are sufficiently precise for the area of application. For sufficiently precise metering in particular, sufficiently precise information about dead volumes and liquid distributions or levels are relevant. Accordingly, all other states, in particular those that cause a loss of liquid or metering precision, are unstable states within the meaning of the invention.

All parameters that characterize at least one specific state are considered, in addition to pressure, further parameters within the meaning of the invention and can be detected as such by suitable sensors and included in the method according to the invention. User interactions as well as control commands or measured data from other devices are considered further parameters as well. Within the meaning of the invention, all detectable parameters may be detected individually or multiple times, parallel or sequentially, as well as automatically or coupled to an event. Models can be generated and adapted from individual or a number of parameters characterizing a specific state or values derived from them, which may be used for a complete or partial description and evaluation of the specific state.

According to the invention, the detection of the pressure or a change in the pressure as an absolute or differential value is performed by means of pressure sensors. Pressure sensors within the meaning of the invention are, in particular to traditional Piezo, resistive, or other MEMS sensors, in particular also such sensors and soft sensors that detect at least one parameter that is different from the pressure and that calculate from this parameter and any other ancillary conditions that are known the pressure, the pressure change, or other values correlating with these parameters. One example for this is the calculation of the pressure through gas equations from measured temperature values and known or measured volumes.

DESCRIPTION WITH REFERENCE TO THE DRAWINGS

FIG. 1 shows a schematic flowchart of the method according to the invention. Methods according to the invention are performed in particular by devices according to the invention for the metering and storing of liquids. At the beginning of the method according to the invention, the device has a start state. Normally, but not necessarily, this start state is the state of the device directly after it was filled with liquid. From the start state, at least one initial pressure detection is performed which is completed with the transition to a stable state and the establishment thereof. Depending on the external conditions, the initial pressure detection may be completed within a few seconds, but may also take significantly longer. Furthermore, depending on the embodiment of the invention, the initial pressure detection may start automatically with the beginning of the method according to the invention, or it may be the result of a user interaction.

After the conclusion of the initialization phase, the system consisting of the device according to the invention and the container content is in a stable state. In a preferred embodiment of the invention, all other process steps are performed either from the stable state or have the objective of maintaining or recreating the stable state. According to the invention, the metering of liquid from the container is performed as needed from the stable state.

According to the invention, a check is performed in regular or irregular intervals as to whether deviations from the stable state have occurred. This is done by at least one current pressure detection, on the basis of which the pressure change between the current pressure and the pressure of the stable state is determined. If no pressure change has taken place, the system continues to be in a stable state. If a pressure change has taken place, however, a reaction is initiated according to the invention which in particular, but not exclusively, has the purpose of recreating the stable state and to therefore prevent or reverse a negative change in the liquid distribution in the container with incorrect metering or metering precision loss.

According to the invention, the current pressure is once more detected after a reaction, in particular to determine the effect of the reaction to the achieving of the stable state. If a pressure change of zero relative to the stable state is found, it was successfully reestablished by the reaction. If there is still, however, a pressure change, the reaction is initiated again.

In a preferred embodiment of the invention, at least one reaction is able to be parameterized depending on the pressure change so that minor pressure changes trigger in particular other or reactions weaker than higher pressure changes.

In a preferred embodiment of the invention, current pressure detections are performed even during an ongoing reaction to be able to parameterize or end the reaction depending on the pressure change.

In a preferred embodiment of the invention, the criterion used to decide for the initiation of a reaction is implemented with a hysteresis behavior to prevent oscillations around the stable state.

In a preferred embodiment of the invention, a current pressure detection is performed after each metering step to ensure that the stable state has been reached after the metering.

In a preferred embodiment of the invention, current pressure detections are performed even during an ongoing metering to predict any reactions that may be necessary after the metering or to improve the precision of the metering.

In some embodiments of the invention, the stable state can be redefined after the current pressure detection in particular, but not exclusively, to take into account various drift effects of the sensors and environmental parameters and the effects of the volume changes of the liquid in the container due to metering.

Figure 2:
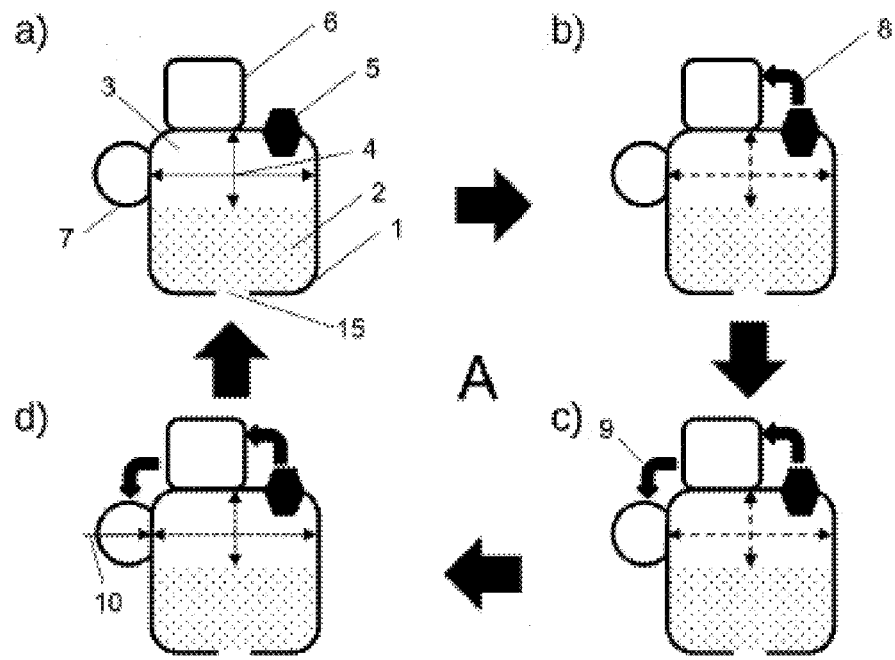
FIG. 2 shows a schematic block diagram of the method according to the invention by using a device according to the invention.
Figure 2:
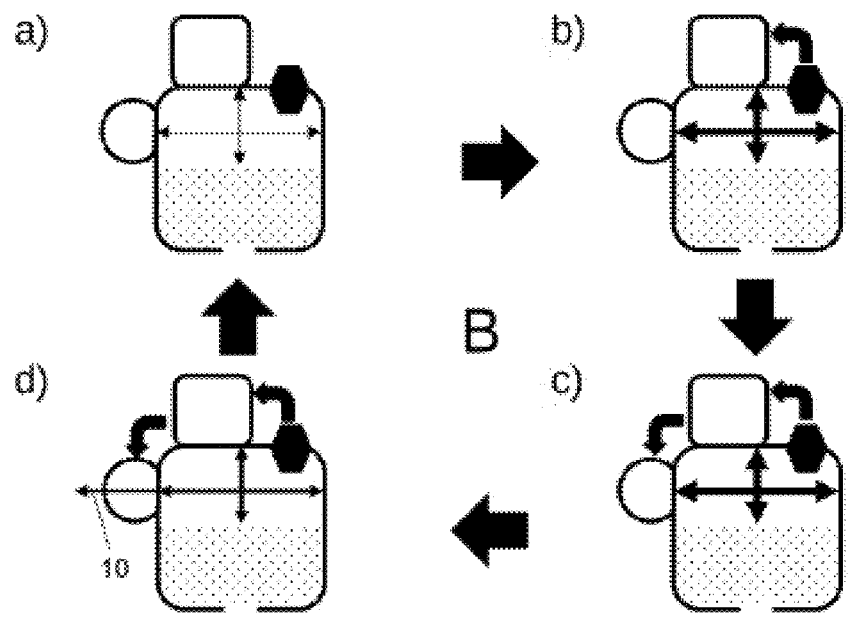

FIG. 2 shows a schematic block diagram of the method according to the invention by using a device according to the invention. FIG. 2 is divided into the two areas A (FIG. 2-A) and B (FIG. 2-B), whereby in FIG. 2-A a negative pressure change (for example due to a cooling of the liquid 2) and in FIG. 2-B a positive pressure change (for example due to a heating of the liquid 2) is detected and corrected by a reaction 9.

According to the invention, the device comprises a container 1 which is at least partially filled with a liquid 2 and which comprises an opening 15 which, according to the invention, is permanently open. In some embodiments of the invention, liquid 2 is permanently found above the opening 15 at the time the method according to the invention is performed.

In a preferred embodiment of the invention, the container 1 comprises furthermore at least a gas phase 3. By the at least one pressure sensor 5, at least one pressure 4 is detected within the container 1. In a preferred embodiment of the invention, at least one pressure 4 of the gas phase 3 is detected by at least one pressure sensor 5.

The device according to the invention furthermore comprises a control unit 6 and at least one liquid transportation device 7, whereby said device may be configured to be active or passive, in particular as a pump or a valve.

FIG. 2 illustrates the application of the method according to the invention by a device according to the invention on the basis of four exemplary partial steps a, b, c, and d, shown in each of the areas A and B. The initialization of the method is not shown here, but partial steps 2-A-a) and 2-B-a) each show the stable state of the entire system after the completion of the initial pressure detection. The metering step was not shown either because a person skilled in the art is familiar with potential metering steps from the stable state (e.g., by opening a valve or by conveying or moving the liquid by means of pumps).

Due to the effect of at least one influencing factor (e.g., temperature), the pressure drops in FIG. 2-A-b (dotted arrows) and the pressure increases in FIG. 2-B-b (bolded arrows). The respective change in the pressure 4 compared to the pressure 4 of the stable state in FIG. 2-A-a or FIG. 2-B-a respectively is detected by the pressure sensor 5 and transmitted to the control unit 6 in the form of pressure values 8. This control unit then initiates, as shown in FIG. 2-A-c and FIG. 2-B-c, at least one reaction 9 which counteracts in particular the pressure change. These kinds of reactions 9 comprise in a preferred embodiment of the invention controlled actions of the liquid transport device 7, in particular, but not exclusively, the opening or closing of at least one valve, the introduction of at least one liquid to the container 1, or the removal of at least one liquid from the container 1 by at least one pump or pump/valve combinations. Due to the respective reaction 9, a pressure compensation 10 occurs in a preferred embodiment of the invention and the pressure 4 in the container 1 normalizes back to the stable state, which is achieved after the completion of at least one reaction 9. Otherwise, at least one further reaction 9 occurs after the next detection of the pressure 4 by the pressure sensor 5, as explained in the process flowchart of FIG. 1.

According to the invention, the reaction 9 in particular, but not exclusively, by the pressure compensation 10 in the container 1 and the corresponding return to the stable state, prevents a redistribution of the liquid 2 within or without the container 1. In FIG. 2-A, for example, a suctioning of liquid 2 into the container 1 is prevented, whereby a negative drop in the metering precision can be counteracted due to the resulting dead volume. In contrast, an expression of parts of the liquid 2 from the container 1 through the opening 15 is prevented in FIG. 2-B, which counteracts an unintended, negative metering process.

Figure 3:
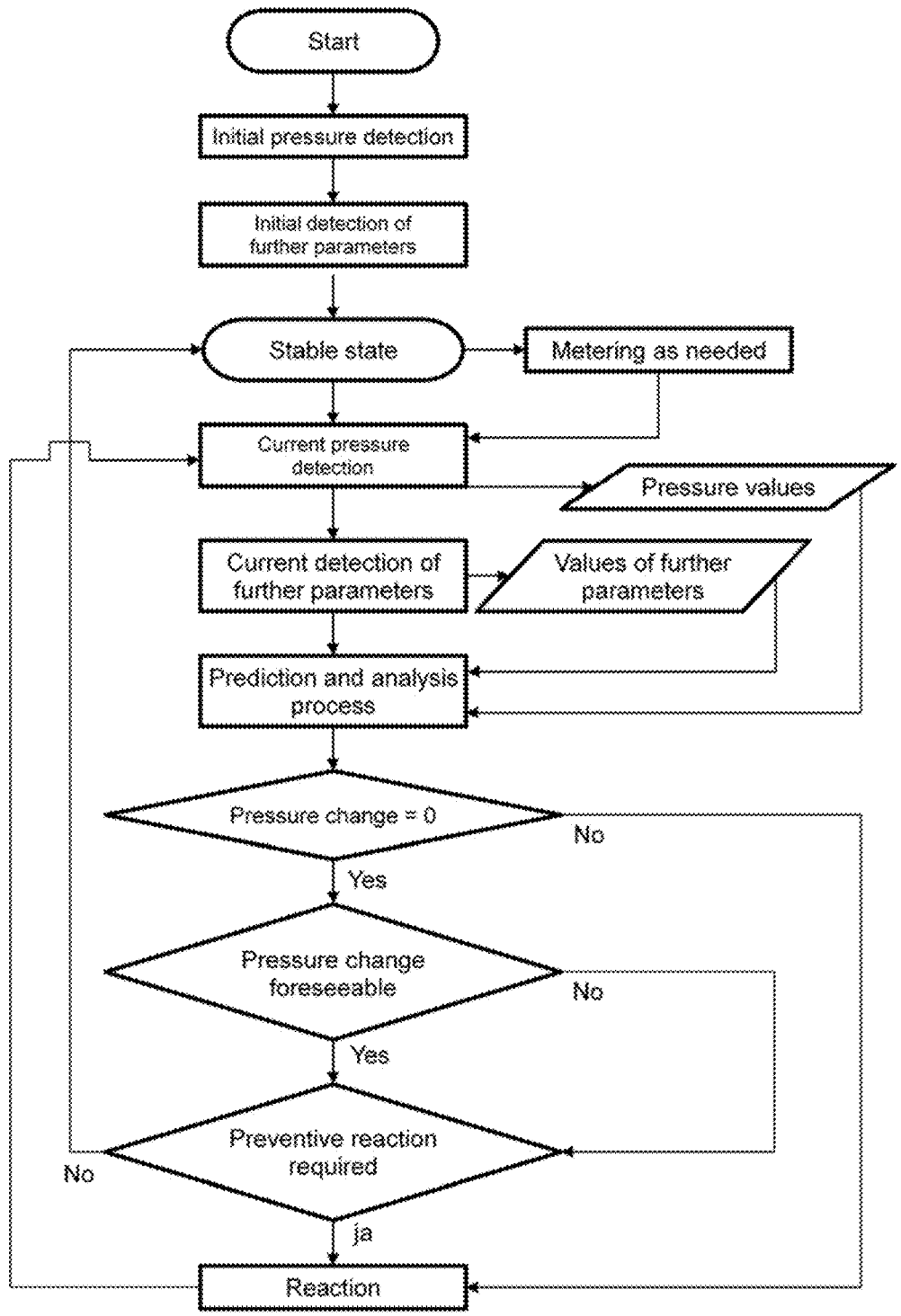
FIG. 3 shows a schematic flowchart of an embodiment of the method according to the invention with additional detection of further parameters as well as with prediction and analysis methods and preventive reaction.

FIG. 3 shows a schematic flowchart of an embodiment of the method according to the invention with an additional detection of further parameters as well as with prediction and analysis methods and preventive reaction. At the beginning of the method according to the invention, the device has a start state. At least one initial pressure detection is performed in the start state. In addition, further parameters are detected by appropriate sensors. All initial pressure and parameter detections may, according to the invention, be performed completely or partially parallel or sequentially.

After the completion of the initialization phase, the system comprising the device according to the invention and the container content is in a stable state. In a preferred embodiment of the invention, all further steps are performed either in the stable state or have the goal of maintaining or recreating the stable state.

According to the invention, the metering of liquid from the container is performed as needed from the stable state. The need is based in particular, but not exclusively, on all previously specified or programmed metering rules, gradients, on interactions of the user with the device according to the invention or devices that control the device according to the invention, and on control commands from other devices that determine the metering need on the basis of measurable parameters.

Both after each metering procedure and directly from the stable state, the current state is checked at regular or irregular intervals to maintain the stable state of the system. According to the invention, at least one current pressure detection is performed. Furthermore, at least one current detection of further parameters is performed in a preferred embodiment according to the invention, whereby all current pressure and parameter detections may, according to the invention, occur completely or partially parallel or sequentially. The resulting current values of the pressure and further parameters are processed by a prediction and analysis process parallel to or subsequent to their detection. In a preferred embodiment of the invention, this is done by at least one control unit which is then formed in particular, but not exclusively, by a computer.

The prediction and analysis processes according to the invention implement in particular, but not exclusively, advantageous prediction methods such as Kalman filters or other Bayesian estimation processes, regression and extrapolation methods, and optimization methods for curve-fitting and model improvement purposes.

In a preferred embodiment of the invention, the prediction and analysis process comprises the development, parameterization, and the optimization of at least one model for the current state of the system as well as for the prediction of future states of the system, whereby, in addition to the pressure, further parameters are advantageously included in the model configuration and optimization as well. In some embodiments of the invention, not only current but also past values are included in the calculation.

According to the invention, the prediction and analysis process provides a comprehensive picture of the current system state, which is the basis on which the decision on the initiation of reactions are made. To this purpose, depending on the parameters and models used, various criteria are examined which may pertain both to specific current, past, or future values and parameters, or that draw information from current, past, or future states of at least one model, and that which, by means of combined or more abstracted or more complex criteria, evaluate the need for the initiation of a reaction. According to the invention, the evaluation of criteria for the initiation of a reaction is performed completely or partially parallel or sequentially.

In some embodiments of the invention, in the case where a change of at least one critical parameter or pressure is detected, the prediction and analysis process may be skilled as well to initiate a reaction more quickly. In the same way in such a case, the ongoing detection of parameters may be suspended in some embodiments of the invention to initiate a reaction more quickly. One example for this is the detection of a strong acceleration of the system (e.g., when walking or when the system is lifted), which could cause parts of the liquid to leave through the opening due to the inertia of the liquid in the container. By directly initiating the reaction (for example a partial or complete suctioning of the gas phase above the liquid by a pump as the liquid transport device), this negative effect caused by the acceleration of the system as the influencing factor can be counteracted.

In a preferred embodiment of the invention, current pressure detections and current detections of other parameters whose values can be processed by at least one analysis and prediction process as well are performed during an ongoing metering as well so that the possibly necessary reactions that follow the metering can be foreseen or the precision of the metering improved.

FIG. 3 shows an example of the sequential evaluation of three criteria of varying complexity. Similar to FIG. 1, it is first determined whether a pressure change was detected. If this is the case, a reaction is initiated. Otherwise, a preferred embodiment of the invention evaluates whether a pressure change in the near or far future is likely. Depending on the result of this evaluation, the decision can then be made as to whether a reaction is necessary as a preventive reaction or whether the state has been reached or maintained. Typical examples for a preventive reaction are in particular all reactions that relate to user input or other data that acts according to plan or that can be modeled. According to the prevention, a defined suctioning of the gas phase above the liquid in the container can preventively pull the liquid deeper into the container subsequent to the user input "system will be carried soon," to avoid any wrong metering or other loss of liquid through the opening due to the jolts experienced from the walking.

In a preferred embodiment of the invention, current pressure detections and detections of other parameters are performed during an ongoing reaction as well so as to parameterize or end the reaction on the basis of the pressure change.

According to the invention, the current pressure as well as further current parameters are detected once again after every reaction to determine whether the stable state has been reached or maintained.

Figure 4:
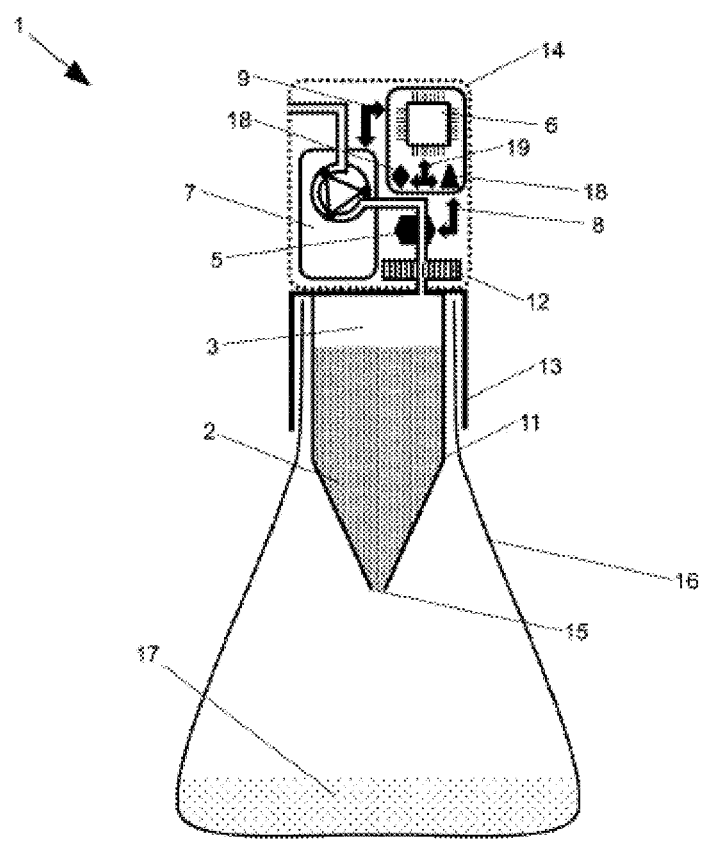
FIG. 4 shows a schematic view of a device according to the invention for the performance of the method according to the invention for the cultivation of cells.

FIG. 4 shows a schematic view of a device according to the invention for the performance of the method according to the invention for the cultivation of cells. The invention is preferably for the cultivation of cells because it permits a controlled addition of substances to the broth culture, in particular, but not exclusively, the addition of nutrients, pH suspending agents, antifoam, and inductors. Here, the device according to the invention that uses the method according to the invention is preferably suitable for guaranteeing the advantages and the simplicity of a metering system that is permanently open at its bottom even under conditions under which it would come to wrong metering, a loss of liquid, or a loss of dosing precision in prior art.

In the embodiment of the invention shown, the metering goes into a shaking flask 16 as a receptacle which is filled, for example, with a broth culture 17. The device according to the invention is placed on it after the receptacle 16 has been filled and firmly attached to the same. The device is there used for the metering and storing of the liquid to be metered.

In a preferred embodiment of the invention, the container 1 is comprised of several components, i.e., a liquid reservoir 11 and a metering device 14. The liquid reservoir 11 as a component of the container 1 has a permanent opening 15 and is at least partially filled with liquid 2 and a gas phase 3, in particular air.

The filling of the liquid reservoir 11 with liquid 2 is performed in some embodiments of the invention through the opening 15, either by using the metering device 14 or by using other suitable devices for the conveyance of liquids.

The liquid reservoir 11 connection with the metering device 14 is gas-tight by means of a sterile filter 12 as a sterility barrier. In a preferred embodiment of the invention, the space below the sterile filter 12 is sterile, whereas the air used according to the invention for the movement or displacement of the liquid 2 above the sterile filter 12 may be nonsterile, in particular since the air itself is sterile after having passed through the sterile filter. Such an embodiment is preferred to take into account the sterility requirements in the application area of the cultivation of cells, since therefore the liquid reservoir 11 may be used as a replaceable, presterilized single-use part, while the metering device 14 can always be nonsterile, which is advantageous in particular regarding the design, material composition, and ease of handling.

In a preferred embodiment of the invention, the liquid reservoir 11 also comprises the lid 13 of the receptacle 16 so that the handling and sterility maintenance are made easier by the production of one piece (e.g., through injection molding).

In a preferred embodiment of the invention, at least one pressure sensor 5 is located in the nonsterile part of the device as a component of the metering device 14. The metering device 14 comprises, in a preferred embodiment of the invention, other sensors 18 for the detection of further parameters, in particular, but not exclusively, user input, temperature, acceleration, liquid level, position, and location. The pressure values 8 and the values of further parameters 19 are, according to the invention, transmitted to at least one control unit 6 which, in a preferred embodiment of the invention, is configured in particular as a computer and which performs the initiation, monitoring, parameterization, and termination of reactions 9.

Metering processes and reactions occur in a preferred embodiment of the invention by the same liquid transport device 7. In the same way, these metering processes and reactions are controlled in a preferred embodiment of the invention by the same control unit 6 as well.

In FIG. 4, the liquid transport device 7 is shown as a pump, in particular as a peristaltic pump that pumps air as the gas phase 3 into the container 1 or sucks it out of the container 1. In this regard, the liquid transport device 7 can also be part of the container 1 which, in the embodiment shown, comprises the liquid reservoir 11, the sterile filter 12, the pressure sensor 5, and parts of the liquid transport device 7, as well as all other connecting pieces between these units that are not mentioned.

The method according to the invention is implemented by the device according to the invention shown in FIG. 4 as follows. For the purpose of metering a liquid 2, the liquid reservoir 11 is filled with liquid 2, connected to the dosing device 14, and then placed on the receptacle 16 filled with the broth culture 17 by means of the lid 13 that is integrated in the liquid reservoir 11.

The initial detection of the pressure and other parameters is initiated here either by a user input after the completion of the installation of the device on the receptacle 16, or it runs from the start and will not reach a stable state until the installation has been completed and the structure comprising the receptacle 16 and the device according to the invention stands still.

Once the stable state has been reached, metering is initiated by the control unit 6 according to user input that was previously or subsequently provided and performed by the peristaltic pump as the liquid transport device 7. To this purpose, air, as the gas phase 3, is pushed through the sterile filter 12 into the fluid reservoir 11 and thereby displaces parts of the liquid 2, which can therefore then be discharged through the opening 15 into the broth culture 17. The pressure sensor 5 detects the pressure of the gas phase 3 after the completion or parallel to each metering and also otherwise at regular or irregular intervals and transmits the resulting pressure values 8 to the control unit 6. In the same way, other sensors 18 detect further parameters and transmit the resulting values 19 to the control unit 6.

According to the invention, the control unit 6 analyzes all values 8/19 received and calculates from them at least one model of the current state as well as future states, if applicable. At least one model is then evaluated to determine the current state on the basis of appropriate criteria and reactions 9 are initiated to maintain or reestablish the stable state depending on the evaluation result. In the exemplary embodiment shown in FIG. 4, the reactions are performed by a peristaltic pump as the liquid transport device 7 through the conveyance of air as the gas phase 3. Below, a few typical states or values are provided together with an exemplary appropriate reaction.

If the pressure that was detected is too high, the liquid transport device 7 will remove, depending on the pressure difference, a certain volume of the gas phase 3 from the container 1 to reestablish the pressure of the stable state. If the pressure that was detected is too low, the liquid transport device 7 will introduce, depending on the pressure difference, a certain volume of the gas phase 3 into the container 1 to reestablish the pressure of the stable state.

If a foreseeable movement of the container 1 was detected due to a user input, the liquid transport device 7 removes a certain volume of the gas phase 3 from the container 1 to draw the liquid 2 upward in the container 1 and to therefore prevent an acceleration-dependent, negative loss in liquid. In the same way, the liquid transport device 7 will return a certain volume of the gas phase 3 into the container 1 as soon as, due to a user input, the end of the foreseeable movement of the container 1 is reached.

If, due to at least one temperature sensor, a change in the ambient temperature is detected, a corresponding change in the temperature of the liquid 2 and of the container 1 is foreseeable as well. The resulting thermodynamic, foreseeable pressure change in the container can be counteracted by a reaction 9 with a preventive pressure compensation (introduction or removal of gas phase 3 into or out of the container 1) by the liquid transport device 7.

LIST OF REFERENCE SIGNS

| | |
|---|---|
| 1 | Container |
| 2 | Liquid |
| 3 | Gas phase, e.g., air |
| 4 | Pressure |
| 5 | Pressure sensor |
| 6 | Control unit |
| 7 | Liquid transport device, passive or active |
| 8 | Pressure values |
| 9 | Reaction |
| 10 | Pressure compensation |
| 11 | Liquid reservoir |
| 12 | Sterile filter |
| 13 | Lid |
| 14 | Metering device |
| 15 | Permanent opening |
| 16 | Receptacle |
| 17 | Broth culture |
| 18 | Further sensors for the detection of further parameters |
| 19 | Values of further parameters |

 State of a device performing the method according to the invention
 Process of the method according to the invention to be performed as a step
 Branch condition over the course of the method according to the invention. What is provided is the respective branch criterion. The
 Value as the data point, data collection, or other manifest information over the course of the method according to the invention
 Direction of the method according to the invention of at least one state, process, value, or other branch condition for at least one state, process, value, or branch condition

What is claimed is:

1. A method for metering and storing liquids by means of a permanently open container, the method comprising:
providing a container comprising:
a liquid reservoir having an opening that is permanently open, the liquid reservoir partially filled with liquid above the opening; and
a metering device positioned outside of the liquid reservoir, the metering device comprising a pump in fluid communication with the liquid reservoir and a pressure sensor configured to monitor gas pressure within the liquid reservoir;
discharging a metered amount of the liquid from the opening;
monitoring gas pressure within the liquid reservoir using the pressure sensor before and after discharging the metered amount of liquid, and if the metering device detects a change in pressure within the liquid reservoir that would cause an unintended discharge of the liquid;
counteracting the change in pressure using the pump by pumping gas into or out of the liquid reservoir to avoid the unintended discharge of the liquid.

2. The method according to claim 1, characterized in that the change in pressure occurs from temperature change of the liquid or movement of the container.

3. The method according to claim 1, characterized in that at least one further parameter is detected and included in a decision-making process counteracting the change in pressure.

4. The method according to claim 1, characterized in that potential future states are predicted on the basis of detected values of the pressure or detected values of further parameters and included in evaluating a need to initiate at least one preventive reaction.

5. The method according to claim 1, characterized in that the discharging of the metered amount is performed by means of movement of a gas phase.

6. The method according to claim 1, characterized in that the discharging of the metered amount of liquid and the counteracting of the change in pressure are controlled by a shared control unit.

7. The method according to claim 1, characterized in that the discharging of the metered amount of liquid and the counteracting of the change in pressure are performed by a shared pump.

8. The method according to claim 1, characterized in that the liquid is discharged into a receptacle through the opening.

9. The method according to claim 8, characterized in that one or more of the steps selected from the group consisting of monitoring the gas pressure and counteracting the change in pressure is performed while the receptacle is being shaken.

10. The method according to claim 8, characterized in that the liquid reservoir includes a lid that is attached to the receptacle.

11. A method for metering and storing liquids by means of a permanently open container, the method comprising:
providing a container comprising:
a liquid reservoir having an opening that is permanently open, the liquid reservoir partially filled with liquid above the opening; and
a metering device fitted in a gas-tight manner to the liquid reservoir, the metering device comprising a pressure sensor configured to monitor pressure within the container and a pump;
discharging a metered amount of the liquid from the opening;
monitoring gas pressure within the liquid reservoir using the pressure sensor, and if the metering device detects a change in pressure within the liquid reservoir that would cause an unintended discharge of the liquid;
adjusting the pressure by pumping gas into or out of the liquid reservoir using the metering device to prevent the unintended discharge of liquid.

12. The method according to claim 11, characterized in that the pressure adjustment counteracts or prevents at least one change of the discharging of the at least one liquid.

13. The method according to claim 11, characterized in that a gas phase is formed within the liquid reservoir and the pressure sensor detects the pressure of the gas phase.

14. The method according to claim 11, characterized in that at least one further parameter is detected and included in a decision-making process about adjusting the pressure.

15. The method according to claim 11, characterized in that potential future states are predicted on the basis of detected values of the pressure or detected values of further parameters and included in an evaluation of the need to initiate a pressure adjustment.

16. The method according to claim 11, characterized in that a targeted movement of the liquid in the container is performed for the purpose of the metering by means of movement of a gas phase.

17. The method according to claim 11, characterized in that the metering and the pressure change are controlled by a shared control unit.

18. The method according to claim 11, characterized in that metering of the liquid and the pressure adjustment are performed by a shared pump.

19. The method according to claim 11, characterized in that the liquid is discharged into a receptacle through the opening.

20. The method according to claim 19, characterized in that one or more of the steps selected from the group consisting of monitoring gas pressure, adjusting the pressure, and discharging the liquid into the receptacle is performed while the receptacle is being shaken.

21. The method according to claim 19, characterized in that the liquid reservoir includes a lid that is attached to the receptacle.

22. A method for metering and storing liquids by means of a permanently open container, the method comprising:
providing a container comprising:
a liquid reservoir having an opening that is permanently open, the liquid reservoir partially filled with liquid above the opening; and
a metering device that is outside of the liquid reservoir, the metering device comprising a pump in fluid communication with the liquid reservoir, a sterile filter, and a pressure sensor configured to monitor gas pressure within the liquid reservoir;
discharging a metered amount of the liquid from the opening;
monitoring pressure within the reservoir using the pressure sensor, and if the metering device detects a change in pressure within the liquid reservoir that would alter the metered amount of liquid during discharge,
counteracting the change in pressure using the pump to avoid altering the metered amount of liquid by pumping gas into or out of the liquid reservoir.

23. The method according to claim 22, characterized in that the step of counteracting the change in pressure prevents a change of the distribution of the liquid.

24. The method according to claim 22, characterized in that a gas phase is formed within the liquid reservoir and the pressure sensor detects pressure of the gas phase.

25. The method according to claim 22, characterized in that at least one further parameter is detected and included in a decision-making process about initiating the counteracting the change in pressure.

26. The method according to claim 22, characterized in that potential future states are predicted on a basis of detected values of gas pressure or detected values of further parameters and included in an evaluation of a need to initiate the counteracting the change in pressure.

27. The method according to claim 22, characterized in that a targeted movement of the liquid in the reservoir is performed for a purpose of metering by means of the movement of a gas phase.

28. The method according to claim 22, characterized in that the discharging and the counteracting the change in pressure are controlled by a shared control unit.

29. The method according to claim 22, characterized in that the discharging and the counteracting the change in pressure are performed by a shared pump.

30. The method according to claim 22, characterized in that the liquid is discharged into a receptacle through the opening.

31. The method according to claim 22, characterized in that one or more of the steps selected from the group consisting of monitoring the pressure, counteracting the change in pressure, and discharging the liquid is performed while the receptacle is being shaken.

32. The method according to claim 30, characterized in that the liquid reservoir includes a lid that is attached to the receptacle.

* * * * *